United States Patent [19]

Nakanishi et al.

[11] Patent Number: 4,851,349
[45] Date of Patent: Jul. 25, 1989

[54] EXPRESSION VECTORS ENCODING CARDIONATRIN AND CARDIODILATIN

[75] Inventors: Shigetada Nakanishi, Kyoto; Yutaka Teranishi, Machida; Kenji Nagahari, Tokyo; Tatsurou Shibiu, Kawasaki; Ken Takamatsu, Tokyo, all of Japan

[73] Assignee: Mitsubishi Chemical Industries Limited, Tokyo, Japan

[21] Appl. No.: 721,579

[22] Filed: Apr. 10, 1985

[30] Foreign Application Priority Data

Apr. 12, 1984 [JP] Japan ............................ 59-73663
Jun. 21, 1984 [JP] Japan ............................ 59-128335
Aug. 16, 1984 [JP] Japan ............................ 59-170739
Oct. 12, 1984 [JP] Japan ............................ 59-213897

[51] Int. Cl.$^4$ .................... C12N 1/20; C12N 1/18; C12N 15/00; C12N 1/00
[52] U.S. Cl. .................... 435/252.33; 435/256; 435/172.3; 435/320; 935/11; 530/324
[58] Field of Search ................ 435/68, 172.3, 253, 435/317, 256, 320; 935/11

[56] References Cited

PUBLICATIONS

Forssmann et al, Biological Abstracts vol. 78, No. 1, p. 260 ab. No. 2250, 1983.
Lazune et al, Chemical Abstracts vol. 101, No. 17, p. 137 ab. No. 144780f, 1984.
Oikawa et al, Nature vol. 309, pp. 724–726, 1984.
Nakayama et al, Nature vol. 310, pp. 699–701 (1984).
Misono et al, Biochem. and Biophys. Res. Comm. vol. 119, pp. 524–529 Mar. 15, 1984.
Kenji et al, Biochem. and Biophys. Res. Comm. vol. 118, pp. 131–139, Jan. 13, 1984.
Flynn et al, Biochem. and Biophys. Res. Comm. vol. 117, pp. 859–865 Dec. 28, 1983.
Currie et al, Science, vol. 223, pp. 67–69 Jan. 6, 1984.
Wallace et al, Nucleic Acids Research vol. 9, pp. 879–894 (1981).
Suggs et al, PNAS USA vol. 78, pp. 6613–6617 Nov. 1981.
Tacon et al, Molec. Gen. Genet vol. 177 pp. 427–438, 1980.

Primary Examiner—Alvin E. Tanenholtz
Attorney, Agent, or Firm—Weiser & Stapler

[57] ABSTRACT

A recombinant DNA vector containing a DNA sequence which encodes a peptide having the physiological properties of cardionatrin and cardiodilatin.

8 Claims, 12 Drawing Sheets

```
5'--TGGCGAGGGACAGACGTAGGCCAAGAGAGGGGAACCAGAGAGGAACCAGAGGGGAGAGACAGAGCAGCAAGCAGTGGATTGCTCCTTGACGACGCCA
            1      SstI                                   10                                              20
         Met Ser Ser Phe Ser Thr Thr Thr Val Ser Phe Leu Leu Leu Leu Ala Phe Gln Leu Leu Gly Gln Thr Arg
      GC ATG AGC TCC TTC TCC ACC ACC ACC GTG AGC TTC CTC CTT TTA CTG GCA TTC CAG CTC CTA GGT CAG ACC AGA
      -1  1                                                                        50
                       RsaI  30
 Ala Asn Pro Met Tyr Asn Ala Val Ser Asn Ala Asp Leu Met Asp Phe Lys Asn Leu Leu Asp His Leu Glu Glu
 GCT AAT CCC ATG TAC AAT GCC GTG TCC AAC GCA GAC CTG ATG GAT TTC AAG AAT TTG CTG GAC CAT TTG GAA GAA
                                            100
  50                            60                                       70
 Lys Met Pro Leu Glu Asp Glu Val Val Pro Pro Gln Val Leu Ser Glu Pro Asn Glu Glu Ala Gly Ala Ala Leu
 AAG ATG CCT TTA GAA GAT GAG GTC GTG CCC CCA CAA GTG CTC AGT GAG CCG AAT GAA GAA GCG GGG GCT GCT CTC
 =150=                                                              =200=
                      MstII   80                               90
 Ser Pro Leu Pro Glu Val Pro Pro Trp Thr Gly Glu Val Ser Pro Ala Gln Arg Asp Gly Gly Ala Leu Gly Arg
 AGC CCC CTC CCT GAG GTG CCT CCC TGG ACC GGG GAA GTC AGC CCA GCC CAG AGA GAT GGA GGT GCC CTC GGG CGG
                                           250
 100    ApaI                                110                                              120
 Gly Pro Trp Asp Ser Ser Asp Arg Ser Ala Leu Leu Lys Ser Lys Leu Arg Ala Leu Leu Thr Ala Pro Arg Ser
 GGC CCC TGG GAC TCC TCT GAT CGA TCT GCC CTC CTA AAA AGC AAG CTG AGG GCG CTG CTC ACT GCC CCT CGG AGC
     300                 PvuII
                         130                                            140
 Leu Arg Arg Ser Ser Cys Phe Gly Gly Arg Met Asp Arg Ile Gly Ala Gln Ser Gly Leu Gly Cys Asn Ser Phe
 CTG CGG AGA TCC AGC TGC TTC GGG GGC AGG ATG GAC AGG ATT GGA GCC CAG AGC GGA CTG GGC TGT AAC AGC TTC
       RsaI                                   400
 -150
 Arg Tyr
 CGG TAC TGA AGATAACAGCCAGGGAGGACAAGCAGGGCTGGGCCTAGGGACAGACTGCAAGAGGCTCCTGTCCCCTGGGGTCTCTGCTGCATTTGT
 -450                                             PstI        HincII
GTCATCTTGTTGCCATGGAGTTGTGATCATCCCATCTAAGCTGCAGCTTCCTGTCAACACTTCTCACATCTTATGCTAACTGTAGATAAAGTGGTTTGA
      550                                                          600
TGGTGACTTCCTCGCCTCTCCCACCCCATGCATTAAATTTAA
       650
```

Fig. 12

```
BamHI        R.B.S.       HindIII   1   Met Asn Pro Met Tyr Asn Ala Val Ser Asn Ala Asp Leu Met Asp Phe Lys
  ↓                          ↓          ATG AAT CCC ATG TAC AAT GCC GTG TCC AAC GCA GAC CTG ATG GAT TTC AAG
G GAT CCT AGG AGG TTT AAG CTT
                                                                              10                            40

Asn Leu Asp His Leu Glu Glu Lys Met Pro Leu Glu Asp Glu Val Val Pro Pro Gln Val Leu Ser Glu Pro
AAT TTG GAC CAT TTG GAA GAA AAG ATG CCT TTA GAA GAT GAG GTC GTG CCC CCA CAA GTG CTC AGT GAG CCG
            20                        30

Asn Glu Ala Ala Gly Ala Ala Leu Ser Pro Leu Pro Glu Val Pro Pro Trp Thr Gly Glu Val Ser Pro Ala Gln
AAT GAA GCG GGG GCT GCT CTC AGC CCC CTC CCT GAG GTG CCT CCC TGG ACC GGG GAA GTC AGC CCA GCC CAG
                                   50                                       60

Arg Asp Gly Gly Ala Leu Gly  |CGG GGC CCC TGG GAC TCC TCT GAT CGA TCT GCC CTC CTA AAA AGC AAG CTG AGG
AGA GAT GGA GGT GCC CTC GGG  ApaI
                    AvaI
                 70

GCG CTG CTC ACT GCC CCT CGG AGC CTG CGG AGA TCC AGC TGC TTC GGG GGC AGG ATG GAC AGG ATT GGA GCC CAG

AGC GGA CTG GGC TGT AAC AGC TTC CGG TAC TGA AGATAACAGCCAGGAGGAGGACAAGCAGGGCTGGGCCTAGGACAGACTGCAAGAG

GCTCCCTGTCCCCTGGGGTCTCTGCTGCATTTGTGTCATCTTGTTGCCATGGAGTTGTGATCATCCCATCTAAGCTGCAGCTTCCTGTCAACACTTCTC

ACATCTTATGCTAACTGTAGATAAAGTGGTTTGATGGTGACTTCCTCCGCCTCTCCCACCCCATGCATTAAATTTAA
             Arg Term Term
             CGG TGA TAG TCG GG
                      *
```

Fig. 13

```
5'---TGGCGAGGGACAGAGACGTAGGCCAAGAGAGGGGAACCAGAGAGGAGGAGACAGAGCAGCAAGCAGTGATTGCTCCTTGACGACGCCA
                                              1                    10                    20
                                              Met Ser Ser Phe Ser Thr Thr Val Ser Phe Leu Leu Leu Ala Phe Gln Leu Gly Gln Thr Arg
   GC ATG AGC TCC TTC TCC ACC ACC GTG AGC TTC CTC CTT TTA CTG GCA TTC CAG CTC CTA GGT CAG ACC AGA
   -1  1                            SstI
                                            RsaI   30                                 40                                    50
   Ala Asn Pro Met Tyr Asn Ala Val Ser Asn Ala Asp Leu Met Asp Phe Lys Asn Leu Leu Asp His Leu Glu
   GCT AAT CCC ATG TAC AAT GCC GTG TCC AAC GCA GAC CTG ATG GAT TTC AAG AAT TTG CTG GAC CAT TTG GAA GAA
                                            100                                         200
   =50                             60                                       70
   Lys Met Pro Leu Glu Asp Glu Val Val Pro Pro Gln Val Leu Ser Glu Pro Asn Glu Glu Ala Gly Ala Ala Leu
   AAG ATG CCT TTA GAA GAT GAG GTG GTC CCC CCA CAA GTG CTC AGT GAG CCG AAT GAA GAA GCG GGG GCT GCT CTC
   =150                 MstII
                                  80                                       90
   Ser Pro Leu Pro Glu Val Pro Pro Trp Thr Gly Glu Val Ser Pro Ala Gln Arg Asp Gly Gly Ala Leu Gly Arg
   AGC CCC CTC CCT GAG GTG CCT CCC TGG ACC GGG GAA GTC AGC GCC CAG AGA GAT GGA GGT GCC CTC GGG CGG
                                  250                                          
           ApaI
            100                               110                            120
   Gly Pro Trp Asp Ser Ser Asp Arg Ser Ala Leu Leu Lys Ser Lys Leu Arg Ala Leu Leu Thr Ala Pro Arg Ser
   GGC CCC TGG GAC TCT GAT CGA TCT GCC CTC CTA AAA AGC AAG CTG AGG GCG CTG CTC ACT GCC CCT CGG AGC
                                            350
                      PvuII
                           130                                  140
   Leu Arg Arg Ser Cys Phe Gly Gly Arg Met Asp Arg Ile Gly Ala Gln Ser Gly Leu Gly Cys Asn Ser Phe
   CTG CGG AGA TCC AGC TGC TTC GGG GGC AGG ATG GAC AGG ATT GGA GCC CAG AGC GGA CTG GGC TGT AAC AGC TTC
             RsaI
   -150
   Arg Tyr
   CGG TAC TGA AGATAACAGCCAGGAGGAGGACAAGCAGGCTGGGCCTAGGACACAGACTGCAAGAGGCTCCTGTCCCCTGTCCCTGGGTCTCTGCTGCATTTGT
        450                                            500             PstI        HincII
                                                                  AGCTTCCTGTCAACACTTCTCACATCTTATGCTAACTGTAGATAAAGTGGTTTGA
                                                                                      600

GTCATCTTGTTGCCATGGAGTTGTGATCATCCCATCTAAGCTGTGATCATCCCATCTAAGCTG
                      550
   TGGTGACTTCCTCCGCCTCTCCACCCCATGCATTAAATTTAA
                      650
```

4,851,349

EXPRESSION VECTORS ENCODING CARDIONATRIN AND CARDIODILATIN

FIELD OF THE INVENTION

This invention relates to an expression vector, DNA fragment, peptide and host which are useful for production of a protein having valuable physiological properties, such as blood pressure depressant activity, as well as to a process for production of such a protein.

DESCRIPTION OF THE PRIOR ART

It has been known that cardionatrin is derived from a precursor protein from the atrium and has Na+ diuretic and vasodilating activities. Cardionatrin is a peptide consisting of 28 amino acids:

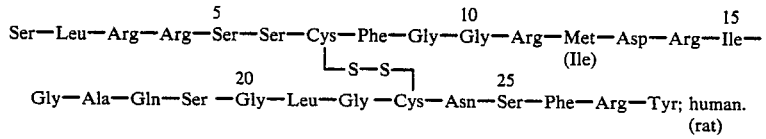

On the other hand, it has also been known that cardiodilatin is a peptide having a molecular weight of approximately 7,500 and derived from a precursor protein from the atrium, and exhibits a muscle relaxant activity.

It has been reported: cardiodilatin derived from swine has the N-terminal sequence of 30 amino acids. See Anatomy and Embryology, 168, 307–313 (1983):

Asn-Pro-Val-Tyr-Gly-Ser-Val-Ser-Asn-Ala-Asp-
    Leu-Met-Asp-Phe-Lys-Asn-Leu-Leu-Asp-His-
    Leu-Glu-Asp-Lys-Met-Pro-Leu-Glu-Asp.

The precursor proteins of these peptides have also been investigated in protein level, but no report has been made in DNA level.

The present inventors have studied in order to establish DNA sequences of such precursor proteins and, accordingly, to obtain a DNA fragment containing the base sequence which codes for the precursor of cardionatrin and also an expression vector suitable for production of a desired protein. Now, we have found that a DNA sequence coding for cardiodilatin is also present in a cDNA fragment containing the DNA sequence which codes for cardionatrin, and attained the present invention.

SUMMARY OF THE INVENTION

This invention provides an expression vector which contains a structural gene coding for cardionatrin and-/or cardiodilatin or a structural gene coding for at least a portion of a cardionatrin-like and/or cardiodilatin-like substance having a physiological activity equivalent to said cardionatrin and/or cardiodilatin.

Also provided according to the invention is a DNA fragment which comprises the base sequence coding for cardionatrin and represented by the following formula (I):

AGC CTG CGG AGA TCC AGC TGC TTC
    GGG GGC AGG ATG GAC AGG ATT GGA
    GCC CAG AGC GGA CTG GGC TGT AAC
    AGC TTC CGG TAC     (I)

or a base sequence coding for a cardionatrin-like substance having a physiological activity equivalent to said cardionatrin.

Further, there is provided according to the invention a DNA fragment which comprises the base sequence coding for cardiodilatin and represented by the following formula (II):

```
AAT CCC ATG TAC AAT GCC GTG TCC AAC GCA GAC CTG ATG GAT TTC   (II)
AAG AAT TTG CTG GAC CAT TTG GAA GAA AAG ATG CCT TTA GAA GAT
GAG GTC GTG CCC CCA CAA GTG CTC AGT GAG CCG AAT GAA GAA GCG
GGG GCT GCT CTC AGC CCC CTC CCT GAG GTG CCT CCC TGG ACC GGG
GAA GTC AGC CCA GCC CAG AGA GAT GGA GGT GCC CTC
``` or a base sequence coding for a cardiodilatin-like substance having a physiological activity equivalent to said cardiodilatin.

The present invention also provides a DNA fragment which comprises both the base sequence coding for cardionatrin and represented by the formula (I) and the base sequence coding for cardiodilatin and represented by the formula (II), or both a base sequence coding for a cardionatrin-like substance having a physiological activity equivalent to said cardionatrin and a base sequence coding for a cardiodilatin-like substance having a physiological activity equivalent to said cardiodilatin.

According to the invention, there is provided cardiodilatin having the following amino acid sequence (III):

(III)
Asn Pro Met Tyr Asn Ala Val Ser Asn Ala Asp Leu Met Asp Phe
Lys Asn Leu Leu Asp His Leu Glu Glu Lys Met Pro Leu Glu Asp
Glu Val Val Pro Pro Gln Val Leu Ser Glu Pro Asn Glu Glu Ala
Gly Ala Ala Leu Ser Pro Leu Pro Glu Val Pro Pro Trp Thr Gly
Glu Val Ser Pro Ala Gln Arg Asp Gly Gly Ala Leu or a cardiodilatin-like peptide having a physiological activity equivalent to said cardiodilatin.

There is also provided in the invention a microbiologically produced cardionatrin having the following amino acid sequence (IV):

Ser Leu Arg Arg Ser Ser Cys Phe Gly Gly Arg Met
    Asp Arg Ile Gly Ala Gln Ser Gly Leu Gly Cys
    Asn Ser Phe Arg Tyr     (IV)

or cardionatrin-like peptide having a physiological activity equivalent to said cardionatrin.

Further, the invention provides a host transformed with the expression vector which contains a structural gene coding for cardionatrin and/or cardiodilatin or a structural gene coding for at least a portion of a cardionatrin-like and/or cardiodilatin-like substance having a physiological activity equivalent to said cardionatrin and/or cardiodilatin, as well as a process comprising culturing such a host and collecting a protein produced.

DESCRIPTION OF THE INVENTION

One particular method for preparation of a cDNA fragment of the invention which comprises the DNA sequence coding for cardiodilatin will be described hereinbelow.

A human heart slice specimen is homogenized with guanidinyl thiocyanate and total RNA is separated by a CsCl equilibrium density-gradient ultracentrifugation: Chirgwin et al., Biochemistry, 18, 5294–5299 (1979). The RNA is purified by an oligo(dT) cellulose column chromatography in any conventional manner to isolate a poly(A)-containing RNA as a mRNA material.

A cDNA library is prepared from the mRNA material by Okayama and Berg's method: Molecular and Cellular Biology, 2, 161–170 (1982).

In summary, a vector primer and an oligo(dG)-tailed linker are prepared from a hybrid plasmid derived from pBR322 and SV40. Then, cDNA is synthesized in the presence of the vector primer and the mRNA material with the aid of a reverse transcriptase. The cDNA is digested with a restriction enzyme, HindIII, and cyclized together with the linker. The mRNA in the cyclized plasmid is substituted by DNA. Thus, a cDNA fragment-containing plasmid is obtained. Thereafter, an *Escherichia coli*, for example, is transformed with the plasmid and an ampicillin-resistant strain is selected.

On the other hand, the following nucleotides, oligo I and oligo II, are synthesized:

```
3'-TAC CTA GCA TAA CC-5' (oligo I)
        G        G
        C        T
        T
        TCT
        C
```

```
3'-TAC CTG GCA TAA CC-5' (oligo II)
        G        G
        C        T
        T
        TCT
        C
```

These probes are complementary to the DNA sequence coding for Met-Asp-Arg-Ile-Gly of cardionatrin:

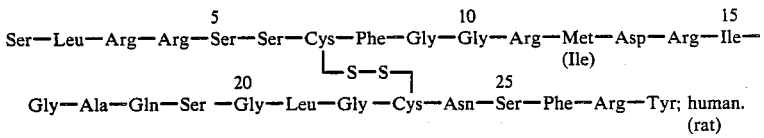

The probes are employed for screening the cDNA library to select clones which hybridize with the probes. A cDNA fragment derived from such a clone is sequenced by the Maxam-Gilbert method: Methods in Enzymology, 65, 499–560 (1980).

The cDNA fragment contains the DNA sequence coding for cardionatrin and/or cardiodilatin according to the invention.

Cardionatrin:

```
AGC CTG CGG AGA TCC AGC TGC TTC GGG GGC AGG ATG GAC AGG ATT    (I)
GGA GCC CAG AGC GGA CTG GGC TGT AAC AGC TTC CGG TAC
```

Cardiodilatin:

```
AAT CCC ATG TAC AAT GCC GTG TCC AAC GCA GAC CTG ATG GAT TTC    (II)
AAG AAT TTG CTG GAC CAT TTG GAA GAA AAG ATG CCT TTA GAA GAT
GAG GTC GTG CCC CCA CAA GTG CTC AGT GAG CCG AAT GAA GAA GCG
GGG GCT GCT CTC AGC CCC CTC CCT GAG GTG CCT CCC TGG ACC GGG
GAA GTC AGC CCA GCC CAG AGA GAT GGA GGT GCC CTC
```

It should be noted that such a cDNA fragment is not limited to the specified nucleotide sequence and the specified number of nucleotide residues. It is contemplated that any nucleotide sequence which may have any substitution(s), deletion(s) and/or addition(s) of nucleotide(s) is all encompassed in the invention, as far as such a DNA sequence codes for a cardionatrin-like and/or cardiodilatin-like substance (peptide) which has a physiological activity (activities) equivalent to that (those) of cardionatrin and/or cardiodilatin.

It should also be noted that such a cDNA fragment is not limited to the aforementioned human-derived fragment but it encompasses all fragments derived from any other higher animals, for example, bovine, swine, horse, mouse, rat or the like.

Further, any ribosome binding site-containing linker, methionine linker, termination linker, or the like may be added to such a DNA fragment to obtain a DNA fragment capable of effecting expression of a desired cardiodilatin-like peptide.

The "cardiodilatin-like substance or peptide" herein means any analogue of cardiodilatin having the same physiological activity (activities) as cardiodilatin per se.

One example of the base sequences coding for a cardiodilatin-like peptide is as follows:

```
Asn  Pro  Met  Tyr  Asn  Ala  Val  Ser  Asn  Ala  Asp  Leu  Met  Asp  Phe        (V)
AAT  CCC  ATG  TAC  AAT  GCC  GTG  TCC  AAC  GCA  GAC  CTG  ATG  GAT  TTC
          |___|
          RsaI

Lys  Asn  Leu  Leu  Asp  His  Leu  Glu  Glu  Lys  Met  Pro  Leu  Glu  Asp
AAG  AAT  TTG  CTG  GAC  CAT  TTG  GAA  GAA  AAG  ATG  CCT  TTA  GAA  GAT
               |_____|
                  AvaII

Glu  Val  Val  Pro  Pro  Gln  Val  Leu  Ser  Glu  Pro  Asn  Glu  Glu  Ala
GAG  GTC  GTG  CCC  CCA  CAA  GTG  CTC  AGT  GAG  CCG  AAT  GAA  GAA  GCG
                                   |_____|
                                      DdeI

Gly  Ala  Ala  Leu  Ser  Pro  Leu  Pro  Glu  Val  Pro  Pro  Trp  Thr  Glu
GGG  GCT  GCT  CTC  AGC  CCC  CTC  CCT  GAG  GTG  CCT  CCC  TGG  ACC  GGG
     |_____|   |_____|         |_____|        |_____|   |_____|
      Fnu4HI        DdeI                MstII             BstNI       HpaII
                                     |_____|   |_____|
                                         BanI              AvaII

Glu  Val  Ser  Pro  Ala  Gln  Arg  Asp  Gly  Gly  Ala  —X
GAA  GTC  AGC  CCA  GCC  CAG  AGA  GAT  GGA  GGT  GCC
                                        |_____|
                                            BanI
``` wherein X represents $\begin{matrix} Leu \\ CTC \end{matrix}$ or $\begin{matrix} Leu & Gly & Arg \\ CTC & GGG & CGG \end{matrix}$.
                                            |_____|
                                                AvaI One example of the DNA fragments containing a base sequence which codes for a cardiodilatin-like peptide comprises the base sequence of the formula (V) coding for a cardiodilatin-like peptide to which a translational initiation codon and translational termination codons are added at the 5'- and 3'-ends, respectively, as shown in the following formula (VI):

```
Met  Asn  Pro  Met  Tyr  Asn  Ala  Val  Ser  Asn  Ala  Asp  Leu  Met  Asp  Phe   (VI)
     AAT  CCC  ATG  TAC  AAT  GCC  GTG  TCC  AAC  GCA  GAC  CTG  ATG  GAT  TTC
               |___|
               RsaI

Lys  Asn  Leu  Leu  Asp  His  Leu  Glu  Glu  Lys  Met  Pro  Leu  Glu  Asp
AAG  AAT  TTG  CTG  GAC  CAT  TTG  GAA  GAA  AAG  ATG  CCT  TTA  GAA  GAT
               |_____|
                  AvaII

Glu  Val  Val  Pro  Pro  Gln  Val  Leu  Ser  Glu  Pro  Asn  Glu  Glu  Ala
GAG  GTC  GTG  CCC  CCA  CAA  GTG  CTC  AGT  GAG  CCG  AAT  GAA  GAA  GCG
                                   |_____|
                                      DdeI

Gly  Ala  Ala  Leu  Ser  Pro  Leu  Pro  Glu  Val  Pro  Pro  Trp  Thr  Gly
GGG  GCT  GCT  CTC  AGC  CCC  CTC  CCT  GAG  GTG  CCT  CCC  TGG  ACC  GGG
     |_____|   |_____|         |_____|        |_____|   |_____|
      Fnu4HI        DdeI                MstII             BstNI       HpaII
                                     |_____|   |_____|
                                         BanI              AvaII

Glu  Val  Ser  Pro  Ala  Gln  Arg  Asp  Gly  Gly  Ala       Op   Am
GAA  GTC  AGC  CCA  GCC  CAG  AGA  GAT  GGA  GGT  GCC  —X—  TGA  TAG
                                        |_____|
                                            BanI
``` wherein X represents $\begin{matrix} Leu \\ CTC \end{matrix}$ or $\begin{matrix} Leu & Gly & Arg \\ CTC & GGG & CGG \end{matrix}$.
                                            |_____|
                                                AvaI This DNA fragment is characterized by an initiation codon at the 5'-end and two termination codons at the 3'-end, and accordingly, a non-fused protein may be obtained in the production of the cardiodilatin-like peptide.

The expression vectors of the invention may be prepared by inserting a DNA fragment, which contains a base sequence coding for cardionatrin and/or cardiodilatin or at least a portion of a cardionatrin-like and/or cardiodilatin-like substance, into a cloning site of an expression vector, which has a regulatory region for expression, such as promoter(s), upstream of said cloning site. Such a promoter may be suitably selected from *E. coli* trp, tac, omp and the like, but not limited to these. Expression vectors derived from a yeast, such as pYK, pGK and the like, may also be employed.

BRIEF DESCRIPTION OF THE DRAWINGS

The preferred embodiments of the invention will be fully described with reference to the drawings. Among the drawings:

FIG. 12 shows the base sequence of the DNA fragment containing the base sequence coding for the cardiodilatin-like peptide in the plasmid phCD shown in FIG. 11; and FIG. 13 shows the base sequence of the DNA fragment obtained in Example 1 hereinbelow, pHANF48, and the amino acid sequence deduced therefrom.

DESCRIPTION OF THE PREFERRED EMBODIMENTS

The expression vector which is suitable for expression in the invention is constructed in the following manner:

(i) Cardionatrin

A plasmid suitable for expression of a fused protein is prepared. Thus, the plasmid contains *E. coli* trp (tryptophan) operon, that is, trp promoter/operator sequence, leader sequence and a portion of the trpE structural gene, and further a plurality of cloning sites linked to said portion of the trpE structural gene. A DNA fragment containing the gene coding for cardionatrin is inserted into one of the cloning sites.

Starting plasmids which may be utilized are those derived from *E. coli* and contained therein in a large number of copies, namely, *E. coli* multi-copy plasmids. Preferably, the plasmids contain an EcoRI restriction site(s) as an insertion site. They include, for example, pBR322, pBR325, pBR327 or the like, but pBR322 is most preferable.

The description hereinafter will be directed to a plasmid containing an EcoRI site(s).

Into an insertion site, that is EcoRI site, there is inserted a fragment containing the trp promoter/operator sequence, the leader sequence and a portion of the trpE structural gene. Such a fragment may be obtained by digesting a gene containing the *E. coli* tryptophan operon with a restriction enzyme, BglII, and forming EcoRI sites at the ends of the fragment containing the trp promoter/operator, the leader sequence and the portion of trpE.

Such a gene containing *E. coli* tryptophan operon includes *E. coli* chromosomal genes. For example, a phage λtrpE-A$_{60-3}$ and a plasmid RSF2124-trp derived from a plasmid RSF2124 (Nagahari et al., Gene, 1, 141–152 (1977)) may preferably be utilized, in consideration of the advantages in the location of the BglII site upstream of the promoter region.

The plasmid RSF2124-trp is digested with BglII. The resulting 2.3 kb BglII fragment contains the trp promoter/operator, the leader sequence and a portion of the trpE structural gene.

EcoRI sites are then formed at both ends of the 2.3 kb fragment. Generally, such sites can be formed by ligating a synthetic linker providing an EcoRI site, namely an EcoRI linker, to the fragment ends.

Alternatively, such an EcoRI fragment can be obtained by introducing the 2.3 kb BglII fragment into a BamHI site of a phage M13mp7 (RF), transforming an *E. coli*, collecting a replicative form (RF) from the transformant, and digesting with the restriction enzyme EcoRI.

Figure 1:
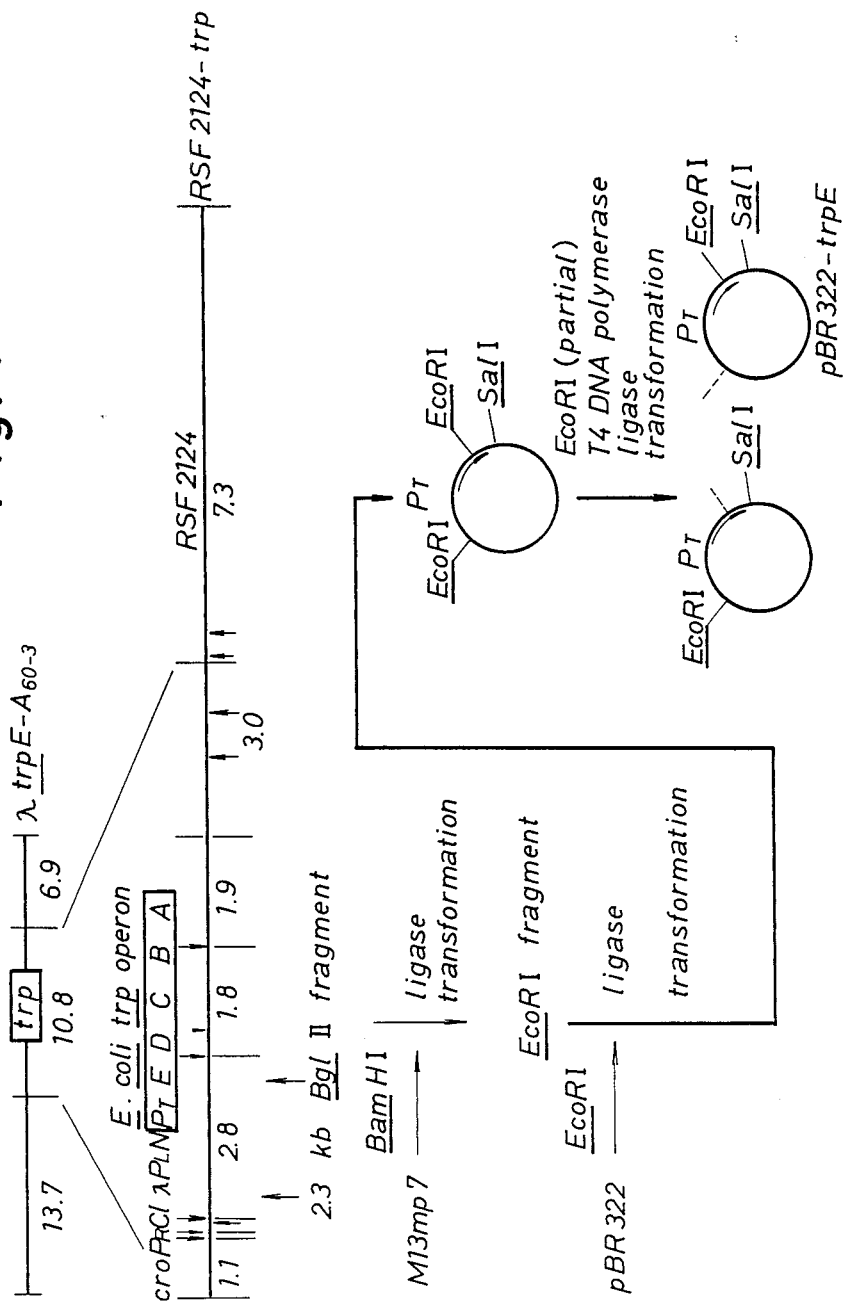
FIGS. 1, 3 and 5 demonstrate the scheme for construction of one example of the plasmids according to the present invention.

The EcoRI fragment having EcoRI sites at both ends is then inserted into an EcoRI site of a starting plasmid, pBR322. An *E. coli* is transformed with the resultant plasmid. The plasmid obtained has EcoRI sites both upstream and downstream of the promoter (P$_T$): FIG. 1. In order to delete the upstream EcoRI site, the plasmid is partially digested with EcoRI, treated with T4 DNA polymerase, ligated with T4 DNA ligase, and used to transform an *E. coli*, and thus a desired 6.6 kb plasmid pBR322-trpE is obtained: FIG. 1.

Figure 2:
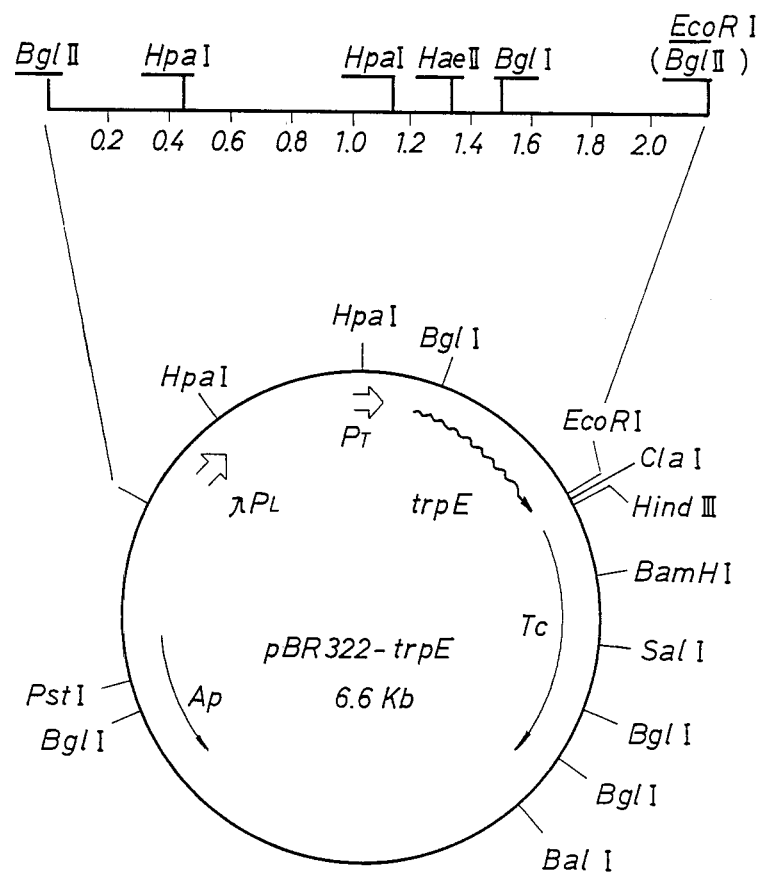
FIG. 2 is the restriction map of the plasmid pBR322-trpE.

FIG. 2 shows the restriction cleavage map of the plasmid pBR322-trpE. In FIG. 2, P$_L$ represents λ phage promoter, Ap is ampicillin resistance, and Tc is tetracycline resistance.

The plasmid pBR322-trpe is partially digested with HpaI and totally with EcoRI to prepare a HpaI-EcoRI fragment containing trpE.

On the other hand, a DNA fragment having a plurality of cloning sites is obtained. For example, a plasmid pUC8 is digested with EcoRI and SalI to obtain a 20 bp EcoRI-SalI fragment having a SmaI restriction site and a BamHI restriction site. At least one of the cloning sites is in phase with the trpE structural gene.

A plasmid pBR322 is digested with EcoRI, treated with T4 DNA polymerase to form blunt ends, and digested with SalI to obtain a larger (EcoRI)-SalI fragment wherein (EcoRI) represents the blunt end.

Figure 3:
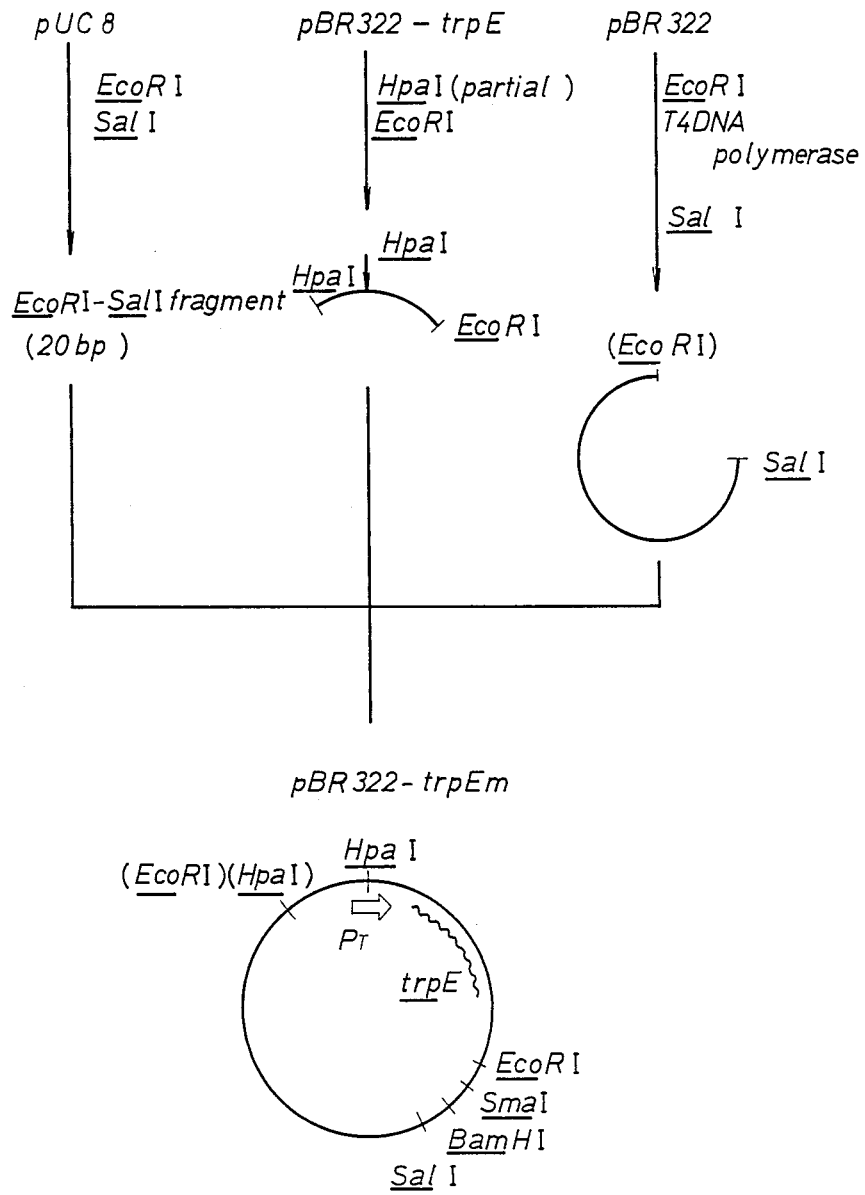

These three fragments, that is, the HpaI-EcoRI fragment, the EcoRI-SalI fragment and the (EcoRI)-SalI fragment are together ligated in the presence of T4 DNA ligase. After transformation of an *E. coli* there is obtained a plasmid pBR322-trpEm: FIG. 3.

The plasmid pBR322-trpEm contains the trp promoter/operator sequence, the leader sequence and a portion of the trpE structural gene. The plasmid further has a plurality of cloning sites, namely, EcoRI, SmaI, BamHI and SalI sites, which are linked to the trpE gene.

The term "linked to" herein means: the cloning sites are linked to the trpE structural gene through a sequence which may code for up to 10 amino acids and contains no stop codon.

The plasmid can be employed as an expression vector for a fused protein by utilizing the multipurpose cloning sites.

Figure 4:
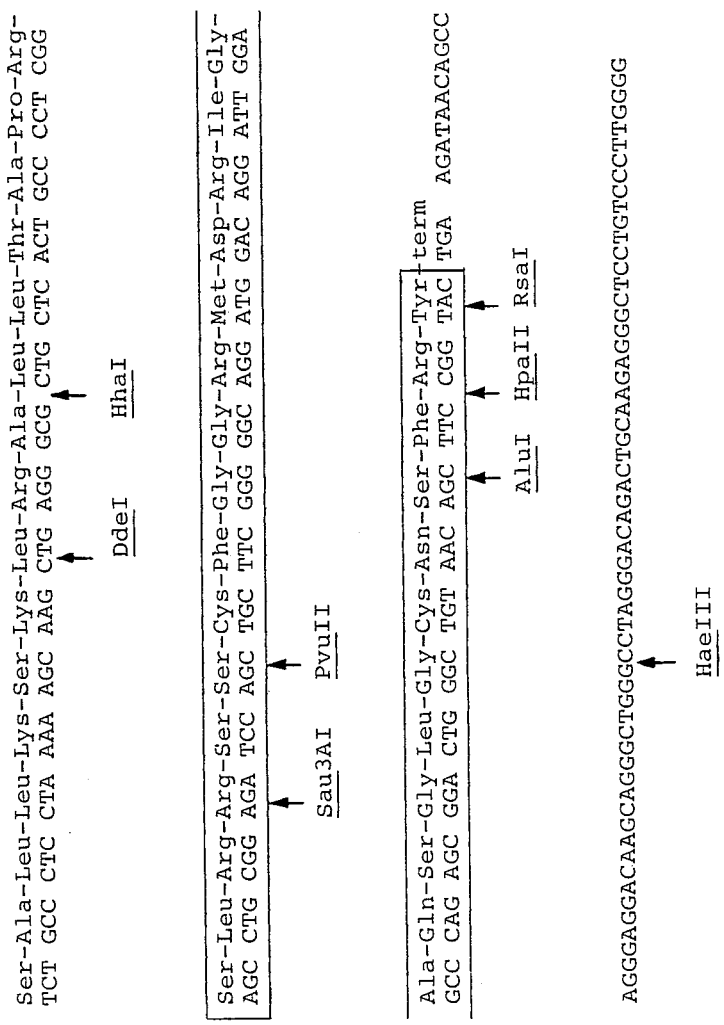
FIG. 4 shows the base sequence of the DNA fragment containing the gene coding for cardionatrin which is employed in the invention, pHANF66, and the amino acid sequence deduced therefrom.

On the other hand, a HaeIII fragment containing the base sequence coding for the amino acid sequence of cardionatrin is obtained from the DNA fragment pHANF66 shown in FIG. 4. Indeed, the DNA fragment is digested with PstI and then with HaeIII to prepare a 190 bp HaeIII fragment containing the gene coding for cardionatrin.

Figure 5:
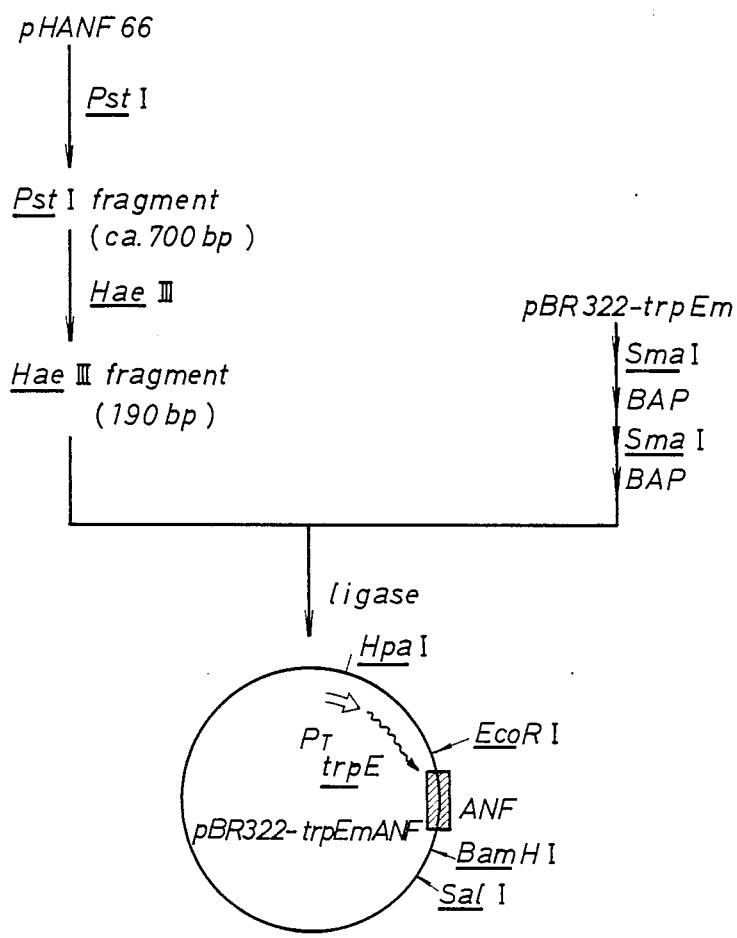

The resultant fragment is inserted into the SmaI site of the pBR322-trpEm and used to transform an *E. coli*. Thus, there is obtained a desired plasmid pBR322-trpEmANF: FIG. 5.

Culture of the transformant incorporating the plasmid pBR322-trpEmANF may produce stably and efficiently a fused protein of cardionatrin.

(ii) Cardiodilatin

A 301 bp fragment containing the sequence coding for cardiodilatin is obtained from a plasmid pHANF48: Nature, 310, 23, 699 (1984). The fragment is ligated with a methionine linker and digested with a restriction enzyme, HindIII, to obtain a 333 bp fragment.

Figure 6:
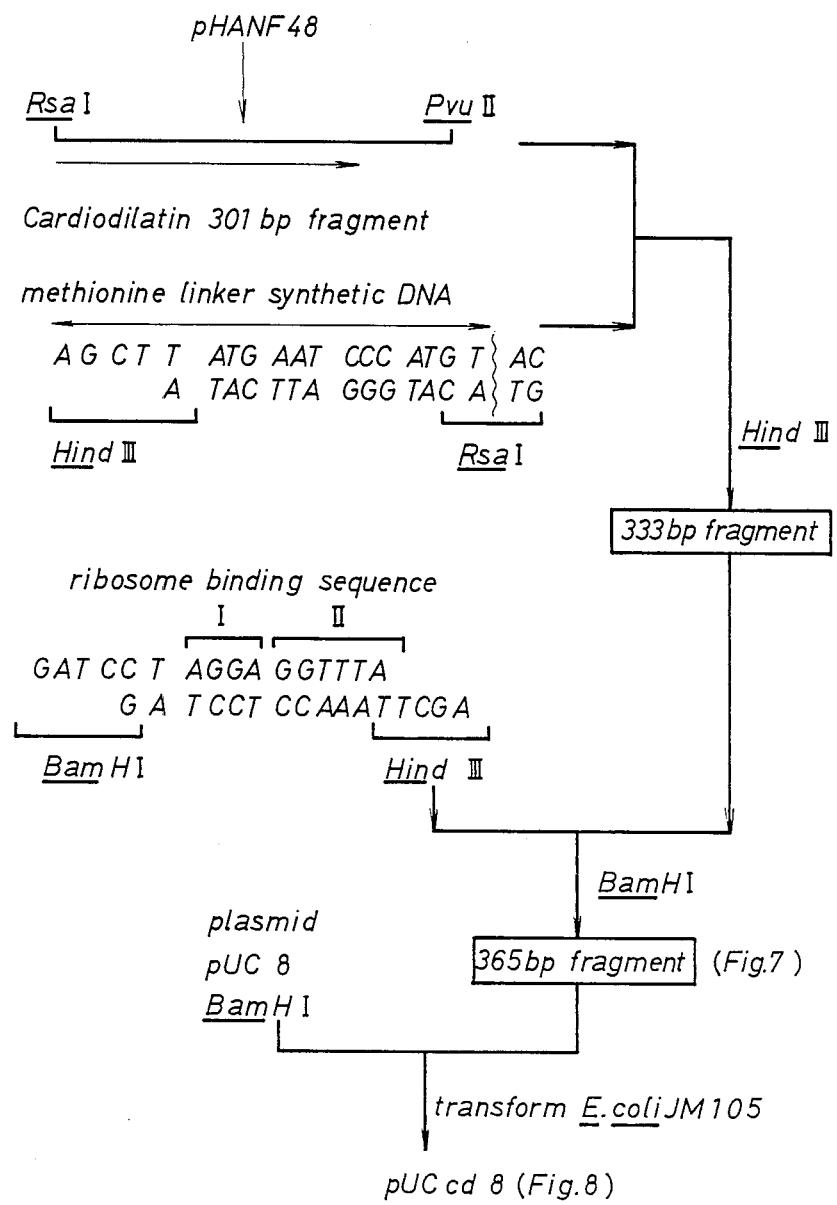
FIGS. 6, 9 and 10 demonstrate the scheme for construction of another example of the plasmids according to the invention.
Figure 7:
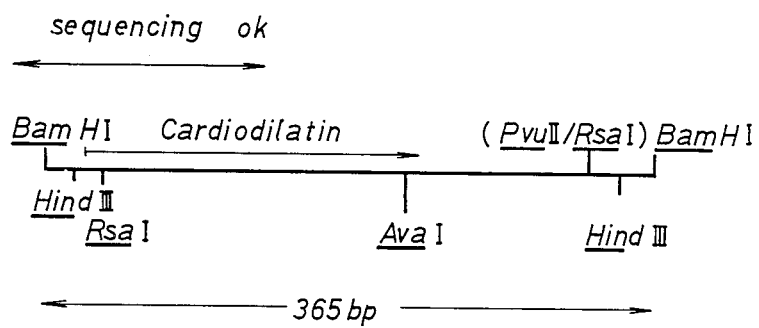
FIG. 7 is the cleavage map of the 365 bp fragment as shown in FIG. 6 by various restriction enzymes.

The 333 bp fragment is ligated with a linker containing a ribosome binding sequence (RBS) shown in FIG. 6, and digested with a restriction enzyme, BamHI, to obtain a 365 bp fragment shown in FIG. 7.

Figure 8:
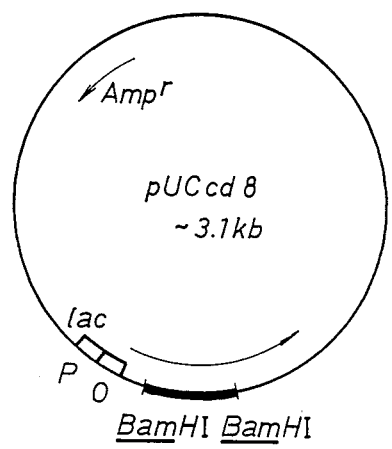
FIG. 8 is the cleavage map of the plasmid pUCcd8.

The 365 bp fragment is inserted into a BamHI site of a plasmid pUC8 purchased from P. L. Biochemicals. After transformation of an *E. coli*, a plasmid pUCcd8 is obtained: FIG. 8.

The plasmid pUCcd8 is partially digested with a restriction enzyme, AvaI, and ligated with a termination linker, namely Term linker:

```
TGA TAG
ACT ATC
```

Figure 9:
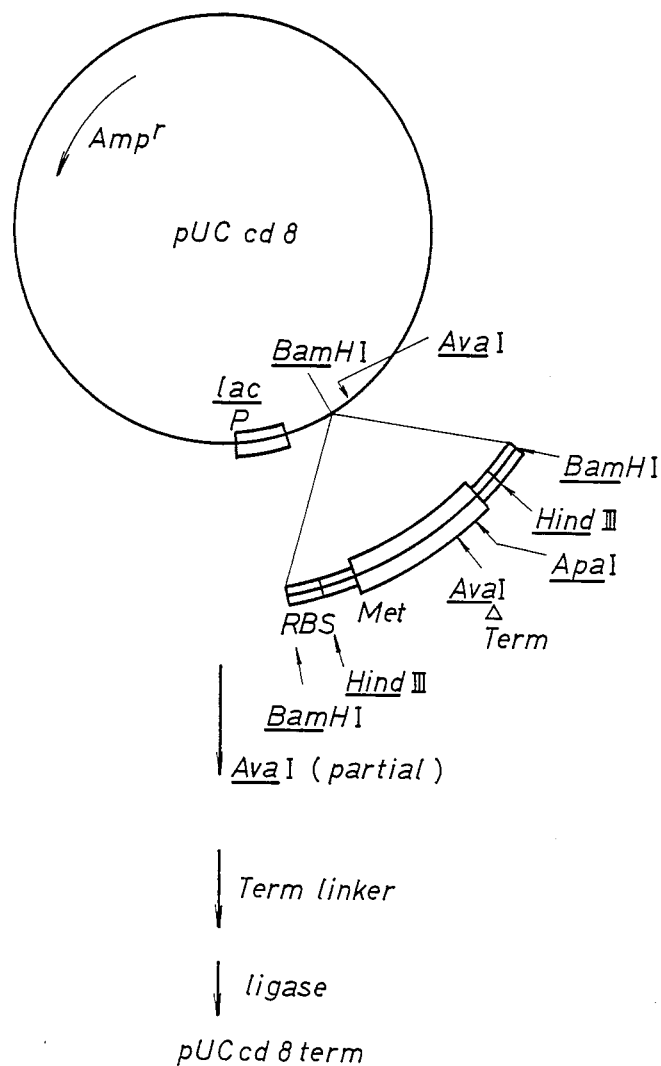

Thus, a plasmid pUCcd8term is obtained: FIG. 9.

Figure 11:
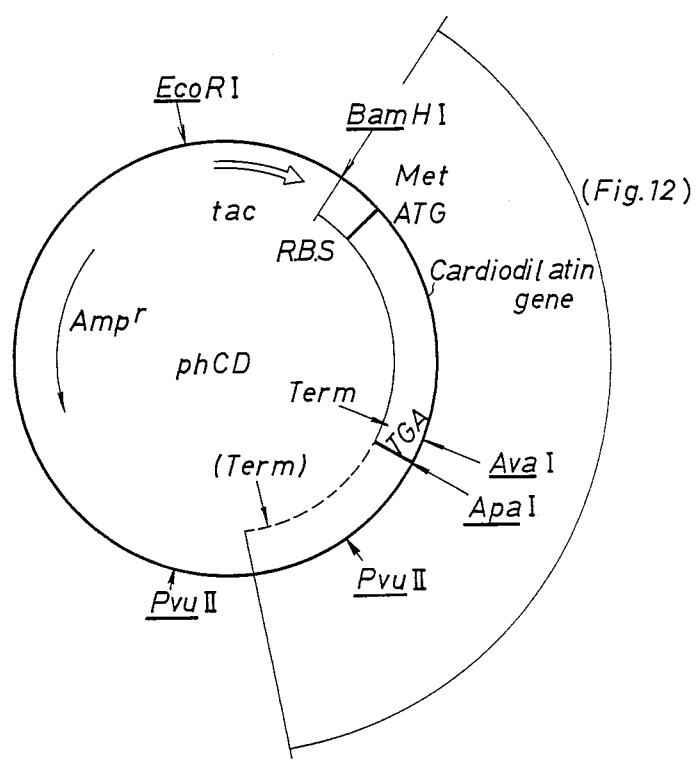
FIG. 11 is the cleavage map of the plasmid phCD.

A plasmid pDR540 purchased from P. L. Biochemicals is digested with EcoRI and BamHI to prepare an approximately 370 bp fragment. On the other hand, the plasmid pUCcd8term is digested with ApaI and BamHI to obtain a 260 bp fragment. Further, the plasmid pHANF48 is digested EcoRI and ApaI to obtain a larger fragment. These three fragments are together ligated and used to transform an *E. coli*. There is obtained a desired expression plasmid, phCD: FIG. 11.

The expression vector of the invention may be introduced into a host. A desired protein can be produced by culturing the transformed host in any conventional manner. The hosts which may be used in the invention include microorganisms, such as *E. coli*, yeast and the like, as well as animal cells.

The protein produced according to the invention is a peptide, that is, cardionatrin represented by the following formula (IV) or cardiodilatin represented by the following formula (III), or a cardionatrin-like or cardiodilatin-like peptide having the same physiological activity as the cardionatrin or cardiodilatin.

(IV)

Ser Leu Arg Arg Ser Ser Cys Phe Gly Gly Arg Met Asp Arg Ile Gly Ala Gln Ser Gly Leu Gly Cys Asn Ser Phe Arg Tyr

-continued (III)

Asn Pro Met Tyr Asn Ala Val Ser Asn Ala Asp Leu Met Asp Phe Lys Asn Leu Leu Asp His Leu Glu Glu Lys Met Pro Leu Glu Asp Glu Val Val Pro Pro Gln Val Leu Ser Glu Pro Asn Glu Glu Ala Gly Ala Ala Leu Ser Pro Leu Pro Glu Val Pro Pro Trp Thr Gly Glu Val Ser Pro Ala Gln Arg Asp Gly Gly Ala Leu

These peptides may exhibit vasodilating (blood pressure depressant), Na+ diuretic and other activities.

EXAMPLES

The invention will be more fully and clearly illustrated with the following non-limiting examples.

Enzymes which were employed in the examples were obtained from New England Biolabs, Inc., USA or Takara Shuzo Co., Ltd., Japan and buffer solutions etc. were according to the manufacturer's recommendation.

EXAMPLE 1

Preparation of cDNA Fragment Containing DNA Sequences Coding for Cardionatrin and Cardiodilatin (1) Human heart slice specimens were ground with liquid nitrogen. An aqueous solution of guanidinium thiocyanate was added to the debris and homogenized. The resulting homogenate was subjected to CsCl equilibrium density-gradient ultracentrifugation in accordance with the method of Chirgwin et al., Biochemistry, 18, 5294–5299 (1979) to isolate total RNA. The total RNA was purified by oligo(dT) cellulose column chromatography in a conventional manner. The isolated poly(A)-containing RNA was used as a mRNA material.

(2) A vector primer and an oligo(dG)-tailed linker were prepared from a hybrid plasmid derived from pBR322 and SV40 in accordance with Okayama and Berg's method described in Molecular and Cellular Biology, 2, 161–170 (1982).

The hybrid plasmid (400 μg) derived from pBR322 and SV40 (0.71–0.86 map unit) was digested with KpnI at 37° C. for 4 hours in a buffer solution containing bovine serum albumin. DNA was recovered by ethanol precipitation in a conventional manner.

The DNA was dissolved in a buffer solution containing dTTP. Terminal deoxy nucleotidyl transferase was added and incubated at 37° C. for 30 minutes. Thus, about 60 dT tail was added to KpnI site. DNA was then recovered by ethanol precipitation.

The DNA was digested with HpaI at 37° C. for 5 hours in a buffer solution containing bovine serum albumin. The larger DNA fragment was purified by agarose gel electrophoresis and recovered by glass powder method: Vogelstein et al., Proc. Natl. Acad. Sci. U.S.A. 76, 615–619 (1979). The DNA was applied to oligo(dA) cellulose column at 0° C., eluted with water, and recovered by ethanol precipitation.

Thus, an oligo(dT)-tailed vectro primer was obtained.

On the other hand, 100 μg of a hybrid plasmid derived from pBR322 and SV40 (0.19–0.32 map unit) was digested with PstI at 37° C. for one hour and a half in a buffer solution containing bovine serum albumin. DNA was recovered and dissolved in a buffer solution containing dGTP. Terminal deoxy nucleotidyl transferase was added and incubated at 37° C. for 20 minutes.

The DNA containing about 10–15 dG tail was recovered and digested with HindIII at 37° C. for one hour in a buffer solution containing bovine serum albumin. The DNA was subjected to 1.8% agarose gel electrophoresis.

Thus, a small oligo(dG)-tailed linker DNA was extracted and recovered.

(3) A cDNA library was obtained in accordance with Okayama and Berg's method: Molecular and Cellular Biology, 2, 161-170 (1982).

There were added 30 μg of mRNA obtained in (1) and 10 μg of the vector primer obtained in (2) into an aqueous solution containing Tris-HCl, pH 8.3, HgCl$_2$, KCl, dithiothreitol, dATP, dTTP, dGTP and [$^{32}$P]dCTP, and incubated at 37° C. for 20 minutes in the presence of reverse transcriptase. Thus, plasmid-cDNA:mRNA was synthesized. This was ethanol precipitated and recovered in the form of pellets.

The pellets were dissolved in a buffer solution containing CoCl$_2$, dithiothreitol, poly(A), [$^{32}$P]dCTP and terminal deoxy nucleotidyl transferase, and incubated at 37° C. for 10 minutes. Thus, dCMP was added to both ends in an amount of 10-15 residues per each end.

The recovered pellets containing the oligo(dc)-tailed plasmid-cDNA:mRNA were dissolved in a buffer solution containing bovine serum albumin, digested with HindIII at 37° C. for one hour, and ethanol precipitated. Thus, HindIII-digested oligo(dC)-tailed cDNA:mRNA plasmid was recovered.

The cDNA:mRNA plasmid was dissolved in a buffer solution containing the oligo(dG)-tailed linker DNA obtained in (2), incubated at 65° C. for 2 minutes and then at 42° C. for 30 minutes, and cooled to 0° C. E. coli DNA ligase was added in the presence of β-NAD (nicotinamide adenine dinucleotide) and incubated overnight. Thereafter, dATP, dTTP, dGTP, dCTP, β-NAD, E. coli DNA ligase, E. coli DNA polymerase and E. coli RNase H were added, incubated at 12° C. for one hour and then at room temperature for one hour, and cooled to stop the reaction. Thus, the desired plasmid containing cDNA fragment was obtained.

The plasmid was used to transform E. coli HB101 in a conventional manner.

(4) On the other hand, two oligonucleotides were synthesized:

```
3'-TAC CTA GCA TAA CC-5' (oligo I)
     G   G
     C   T
     T
     TCT
     C 3'-TAC CTG GCA TAA CC-5' (oligo II)
     G   G
     C   T
     T
     TCT
     C
```

These oligomers were complementary to the DNA sequence coding for Met-Asp-Arg-Ile-Gly of cardionatrin.

These oligo I and II were used as a probe for screening the cDNA library. Twelve clones which hybridized with the probes were selected from 40,000 transformants, and cDNA fragments were extracted from the clones. The restriction enzyme map of the cDNA fragment was established and sequencing of the fragments, pHANF48 and pHANF66, was performed in accordance with the Maxam-Gilbert method: Methods in Enzymology, 65, 499-560 (1980).

FIG. 13 shows the base sequence of the cDNA fragment (pHANF48) and the amino acid sequence deduced therefrom, as well as the cleavage sites of restriction enzymes. In FIG. 13, the doubly framed sequence corresponds to cardiodilatin consisting of 72 amino acid residues and the singly framed sequence corresponds to cardionatrin.

The DNA sequence of cardiodilatin was deduced from the fact that the number of amino acid residues was estimated at 72-75 from its molecular weight of 7,500, and also from the locations of arginines which are readily processed in the living body.

As compared with the swine-derived cardiodilatin described in Anatomy and Embryology, 168, 307-313 (1983), the human-derived cardiodilatin has four different amino acids in the N-terminal sequence of 30 amino acids.

FIG. 4 shows the base sequence of the DNA fragment pHANF66 and the amino acid sequence deduced therefrom, as well as the cleavage sites of restriction enzymes. In FIG. 4, the singly framed sequence corresponds to cardionatrin.

EXAMPLE 2

Preparation of Plasmid pBR322-trpEm (Ia) Construction of Plasmid pBR322-trpE (FIG. 1)

Plasmid RSF2124-trp described in Gene 1, 141-152 (1977) was digested with BglII at 37° C. for one hour and electrophoresed on 1% agarose to obtain 2.3 kb BglII fragment.

Phage M13mp7, 7238 bp, from Bethesda Research Laboratories, Inc., USA, was digsted with BamHI at 37° C. for one hour and ligated with the 2.3 kb BglII fragment at 15° C. for 14 hours in the presence of T4 DNA ligase. E. coli JM103 by Bethesda Research Laboratories, Inc., USA was transformed and transformants were selected by the color change from blue to white of X gal. RF was taken from the transformant and digested with EcoRI at 37° C. for one hour to obtain an EcoRI fragment.

The EcoRI fragment contained trp promoter/operator, leader sequence and a portion of trpE structural gene and had EcoRI sites at both ends.

Plasmid pBR322 was digested with EcoRI at 37° C. for one hour and ligated with the EcoRI fragment at 15° C. for 14 hours in the presence of T4 DNA ligase. E. coli HB101 was transformed and a plasmid having EcoRI sites both upstream and downstream of the promoter (P$_T$) was obtained from the transformant (FIG. 1).

The plasmid was partially digested with EcoRI at 37° C., incubated at 37° C. for 30 minutes in the presence of T4 DNA polymerase and ligated at 15° C. for 14 hours in the presence of T4 DNA ligase. E. coli HB101 was transformed and the desired plasmid pBR322-trpE was obtained (FIG. 1).

This 6.6 kb plasmid had an EcoRI site downstream of P$_T$. The restriction map of the plasmid is shown in FIG. 2.

(Ib) Preparation of HpaI-EcoRI fragment containing trpE (FIG. 3)

The plasmid pBR322-trpE obtained in (Ia) was partially digested with HpaI at 37° C. for 30 minutes and digested with EcoRI at 37° C. for 2 hours. Thus, HpaI-EcoRI fragment containing trpE was obtained.

(II) Preparation of 20 bp EcoRI-SalI fragment from pUC8

Plasmid pUC8 was digsted with EcoRI and SalI at 37° C. for 2 hours to obtain a desired fragment containing a plurality of multipurpose cloning sites.

(III) Preparation of (EcoRI)-SalI fragment from plasmid pBR322

Plasmid pBR322 was digested with EcoRI at 37° C. for 2 hours, incubated at 37° C. for one hour in the presence of T4 DNA polymerase to convert the EcoRI sites in blunt ends, and digested with SalI at 37° C. for 2 hours. Thus, a large (EcoRI)-SalI fragment, 3693 bp, was obtained.

(IV) Construction of pBR322-trpEm

Three fragments obtained in (Ib), (II) and (III) were ligated at 15° C. for 14 hours in the presence of T4 DNA ligase.

The resulting circular plasmid was used to transform E. coli HB101. Plasmid DNA was prepared from the transformant by Helensky's method: Biochemistry, 22, 4428–4440 (1970). Analysis of the base sequence of the DNA by the Maxam-Gilbert method confirmed the desired DNA, that is, plasmid pBR322-trpEm.

EXAMPLE 3

Construction of Plasmid pBR322-trpEmANF (I) Preparation of 190 bp HaeIII fragment of pHANF66

The fragment pHANF66 (50 µg) obtained in Example 1 was digested with PstI at 37° C. for 2 hours and subjected to polyacrylamide gel electrophoresis. About 700 bp fragment was extracted from the gel, digested with HaeIII at 37° C. for 2 hours and subjected to polyacrylamide gel electrophoresis. A fragment (190 bp) was extracted (FIG. 5).

(II) SmaI digestion of pBR322-trpEm

Plasmid pBR322-trpEm (10 µg) was digsted with SmaI at 37° C. for 3 hours and treated with alkaline phosphatase (BAP) at 37° C. for 30 minutes. These procedures were repeated twice (FIG. 5).

(III) Construction of pBR322-trpEmANF (FIG. 5)

Two fragments obtained in (I) and (II) were ligated at 15° C. for 14 hours in the presence of T4 DNA ligase. The circular DNA was used to transform E. coli HB101. Plasmid DNA was prepared from the resulting transformant in a conventional manner and sequencing was performed by the Maxam-Gilbert method.

E. coli transformed with plasmid pBR322-trpEmANF was cultured in M9CA medium (Molecular Cloning; Cold Spring Harbor Laboratories, 1982, p. 441). The culture medium was subjected to 10% SDS-polyacrylamide gel to analyze fused proteins. An expected band of a peptide consisting of 378 amino acid residues (about 40 kilo daltons) was confirmed in the gel stained by Coomassie Brilliant Blue R.

EXAMPLE 4

Construction of Plasmid phCD

The plasmid pHANF48 was digested with PvuII and RsaI to obtain 301 bp fragment containing the gene for cardiodilatin. The 301 bp fragment was ligated with methionine linker at 8° C. for 14 hours in the presence of T4 DNA ligase and digested with HindIII at 37° C. for 2 hours. The resulting 333 bp fragment was ligated with the linker of FIG. 6 containing the ribosome binding sequence at 8° C. for 14 hours in the presence of T4 DNA ligase, and digested with BamHI at 37° C. for 2 hours. Thus, 365 bp fragment shown in FIG. 7 was obtained.

On the other hand, plasmid pUC8 was digsted with BamHI at 37° C. for 2 hours. The 365bp fragment was inserted into this BamHI site.

E. coli JM105 was transformed and white colonies on X gal were selected. Thus, plasmid pUCcd8 was obtained: FIG. 8.

The plasmid pUCcd8 was digsted with AvaI (partial) at 37° C. for 30 minutes and ligated with the termination (Term) linker containing stop codons in the presence of T4 DNA ligase. Thus, plasmid pUCcd8term was obtained: FIG. 9.

Figure 10:
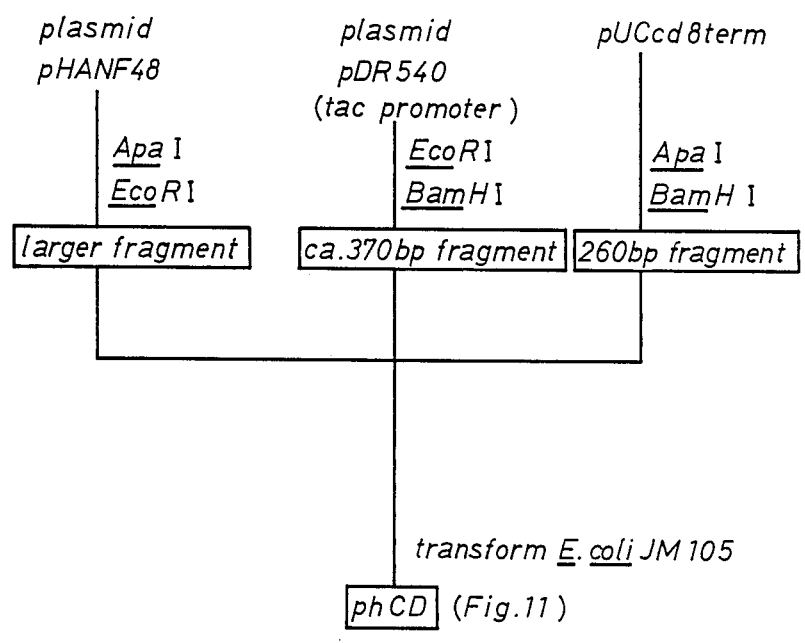

Plasmid pDR540 containing tac promoter was digested with EcoRI and BamHI at 37° C. for 2 hours to obtain about 370 bp fragment: FIG. 10. On the other hand, the plasmid pUCcd8term was digested with ApaI and BamHI at 37° C. for 2 hours to obtain 260 bp fragment: FIG. 1. Further, pHANF48 was digested with ApaI and EcoRI to obtain a large fragment containing the ampicillin resistance gene: FIG. 10.

Three fragments were ligated at 8° C. for 14 hours in the presence of T4 DNA ligase. The resulting plasmid was used to transform E. coli JM105 and plasmid phCD was obtained from the transformant: FIG. 11.

Production of Cardiodilatin-like Peptide

E. coli JM105 transformed with the plasmid phCD was cultured in M9-CA medium. Production of a cardiodilatin-like peptide having a molecular weight of approximately 7,500 was confirmed by sequencing the N-terminal amino acids.

The amino acid sequence of the peptide is shown below:

Met Asn Pro Met Tyr Asn Ala Val Ser Asn
Ala Asp Leu Met Asp Phe Lys Asn Leu Leu
Asp His Leu Glu Glu Lys Met Pro Leu Glu
Asp Glu Val Val Pro Pro Gln Val Leu Ser
Glu Pro Asn Glu Glu Ala Gly Ala Ala Leu
Ser Pro Leu Pro Glu Val Pro Pro Trp Thr
Gly Glu Val Ser Pro Ala Gln Arg Asp Gly
Gly Ala Leu Gly Arg.

What is claimed is:

1. A recombinant DNA vector which contains a DNA sequence which codes for a peptide which has the diuretic and vasodilating physiological properties of cardionatrin and for a peptide which has the muscle relaxant physiological property of cardiodilatin, and which is shown in FIG. 13, the singly framed sequence corresponding to the first peptide and the double-framed sequence corresponding to the second peptide.

2. The recombinant DNA vector of claim 1 which is an expression vector and which contains a promoter operably linked to regulate the expression of the sequence.

3. The expression vector of claim 2 wherein the promoter is selected from the group consisting of trp, tac, and omp.

4. The expression vector of claim 3 which comprises the trp promoter/operator sequence and a portion of the trpE structural gene.

5. The expression vector of claim 4 wherein the linking of the cloning sites to the trpE gene is through a base sequence which codes up to 10 amino acids and contains no stop codon.

6. The vector of claims 2, 3, 4 or 5 which is a plasmid.

7. A microorganism host transformed with a vector of claims 2, 3, 4 or 5.

8. The microorganism of claim 7 which is *E. coli* or yeast.

* * * * *

Notice of Adverse Decisions in Interference

In Interference No. 102,464, involving Patent No. 4,851,349, S. Nakanishi, Y. Teranishi, K. Nagahari, T. Shibui, K. Takamatsu, EXPRESSION VECTORS ENCODING CARDIONATRIN AND CARDIODILATIN, final judgment adverse to the patentees was rendered Oct. 10, 1991, as to claims 1-8.

*(Official Gazette December 24, 1991)*.